(12) United States Patent
Vallittu et al.

(10) Patent No.: US 7,435,764 B2
(45) Date of Patent: Oct. 14, 2008

(54) PREPREG AND ITS USE

(75) Inventors: Pekka Vallittu, Kuusisto (FI); Antti Yli-Urpo, Littoinen (FI); Lippo Lassila, Lielax (FI); Timo Närhi, Helsinki (FI); Tuomas Waltimo, Turku (FI)

(73) Assignee: Stick Tech Oy, Turku (FI)

( * ) Notice: Subject to any disclaimer, the term of this patent is extended or adjusted under 35 U.S.C. 154(b) by 406 days.

(21) Appl. No.: 10/558,274

(22) PCT Filed: May 21, 2004

(86) PCT No.: PCT/FI2004/000309

§ 371 (c)(1),
(2), (4) Date: Nov. 23, 2005

(87) PCT Pub. No.: WO02/100355

PCT Pub. Date: Dec. 19, 2002

(65) Prior Publication Data

US 2007/0054244 A1    Mar. 8, 2007

(30) Foreign Application Priority Data

May 23, 2003   (FI) ................................. 20030780

(51) Int. Cl.
*A61K 6/083* (2006.01)
*A61C 5/00* (2006.01)

(52) U.S. Cl. ....................... 523/117; 523/120; 433/215; 433/228.1

(58) Field of Classification Search ................. 523/117, 523/120; 433/215
See application file for complete search history.

(56) References Cited

U.S. PATENT DOCUMENTS

| | | | | |
|---|---|---|---|---|
| 5,846,640 A | * | 12/1998 | Vallittu | 428/306.6 |
| 5,891,233 A | | 4/1999 | Salonen et al. | 106/35 |
| 5,902,755 A | * | 5/1999 | Driggett et al. | 442/172 |
| 6,186,790 B1 | | 2/2001 | Karmaker et al. | 433/215 |
| 6,197,410 B1 | | 3/2001 | Vallittu et al. | 428/292.1 |
| 6,299,930 B1 | | 10/2001 | Marotta et al. | 427/2.28 |
| 6,596,373 B1 | * | 7/2003 | Kishi et al. | 428/116 |
| 6,616,971 B2 | * | 9/2003 | Evans | 427/249.3 |
| 2003/0068598 A1 | | 4/2003 | Vallittu et al. | 433/167 |

FOREIGN PATENT DOCUMENTS

WO    WO 02/100355    12/2002

* cited by examiner

*Primary Examiner*—Tae H Yoon
(74) *Attorney, Agent, or Firm*—James C. Lydon

(57) ABSTRACT

The invention relates to a prepreg comprising a base part, said base part comprising fibers and a matrix, said matrix being at least partially uncured. The prepreg is characterized in that it further comprises a surface part consisting essentially of bioactive filler material, said bioactive filler material being in particle form and at least partially and at most partially embedded in said base part. The invention also relates to a composite obtainable by curing said prepreg. The invention further relates to a mineralizing sheet for treatment of hypersensitive teeth and to the use of said prepreg and composite.

11 Claims, 7 Drawing Sheets

PREPREG AND ITS USE

FIELD OF THE INVENTION

This invention relates to a prepreg comprising a base part, said base part comprising fibers and a matrix, said matrix being at least partially uncured. The invention further relates to a composite and a mineralizing sheet for treatment of hypersensitive teeth as well as to the use of said prepreg and composite.

BACKGROUND OF THE INVENTION

The publications and other materials used herein to illuminate the background of the invention, and in particular, the cases to provide additional details respecting the practice, are incorporated by reference.

The use of reinforced composites made of particulate fillers or reinforcing fibers has gained popularity in dental and medical field. Recently, several inventions regarding the fiber-reinforced composites have been made. The state-of-the-art fiber-reinforced composites yield high strength properties and by selecting the multiphase resin matrix for the composite, the handling characteristics of the composite can be considerably improved. Such products are disclosed for example in U.S. Pat. No. 6,197,410 and WO 02/100355.

On the other hand, a lot of development with bioactive materials, namely bioactive glass, sol-gel processed silica, hydroxyapatite and Ca/P -doped silica has occurred. These materials can be used to biomineralize the surface of the dentine of tooth, or to achieve attachment of bone to biomaterials surface. The mineralization of the dentine is used in order to eliminate the hypersensitiveness of the tooth due to opened dentinal tubules. The elimination of the hypersensitiveness occurs by sealing the tubules with apatite-like minerals by means of bioactive glass granules, for example. The biomineralization of the dentine takes several days or weeks to occur. During this time, the bioactive glass granules should be located in contact with the dentine. This has caused practical problems, because the bioactive granules need to hold on place with various types of materials, like surgical pastes. This kind of paste is disclosed for example in U.S. Pat. No. 5,891,233.

Another use for biomineralization of the dentine is the use of bioactive glass granules as filling material of the tooth. The biomineralization hardens the dentine surface and allows better bonding of filling composite resins to dentine. In addition, the bioactive granules behave as antimicrobial agent in bone sinuses and in root canal.

The shortcoming of methods to use bioactive glass granules on dentine is the difficulties in application, as explained above. The currently used application methods of bioactive materials are limited in their use, mainly because the bioactive material does not remain on the tooth surface for enough long period of time, or when some pastes, such as surgical pastes have been used to cover the bioactive material, cosmetic and esthetic problems and discomfort for the patient has occurred.

In orthopedics, fillers materials as bioactive glass have been used successfully.

OBJECTS AND SUMMARY OF THE INVENTION

The object of this invention is to provide a material that can be used to mineralize dentine tubules, a material that is easy to use and that does not cause any discomfort for the patient.

A further object of this invention is to provide an improved material for use as filling material for teeth, as well as for other dental and medical applications.

The objects of the present invention are fulfilled by the prepreg according to the present invention. Said prepreg comprises a base part, said base part comprising fibers and a matrix, said matrix being at least partially uncured, and said prepreg is characterized in that it further comprises at least one surface part consisting essentially of bioactive filler material, said bioactive filler material being in particle form and at least partially and at most partially embedded in said base part.

The objects of the present invention are further fulfilled by the composite obtainable by curing the prepreg according to the invention as well as by the mineralizing sheet for treatment of hypersensitive teeth according to the present invention and by the use of the present prepreg and composite in various dental and medical applications, as will be discussed more in detail below.

DETAILED DESCRIPTION OF THE INVENTION

The invention is disclosed in the appended independent claims.

The prepreg according to the invention is characterized in that it comprises at least one surface part consisting essentially of bioactive filler material, said bioactive filler material being in particle form and at least partially and at most partially embedded in said base part.

In this application, by curing it is meant polymerization and/or crosslinking. By matrix, it is understood the continuous phase of the composition and by uncured matrix it is meant a matrix that is in its deformable state but that can be cured, i.e. hardened, to a non-deformable state. The uncured matrix may already comprise some long chains but it is essentially not yet polymerized and/or crosslinked. By prepreg, it is meant a semi-manufactured product, that is, a product that is not polymerized or partly polymerized yet still deformable. The polymerization of a prepreg leads to a composite. The terms "composite" and "cured prepreg" may be used interchangeably.

The objects of this invention are thus fulfilled, i.e. the invention provides a material, a prepreg, which can be used to mineralize and disinfect dentine tubules, that is easy to use and that does not cause any discomfort for the patient This invention also provides an improved material for use as filling material for teeth, as well as for other dental and medical applications, as will be described more in detail below.

The present invention provides a prepreg for manufacturing a composite material consisting of a fiber-reinforced part and a surface of bioactive fillers. At least one surface of the fiber-matrix system is coated with a layer of bioactive substance. It is also possible to have the resin matrix in partly polymerized form. The bioactive substance is in the form of particulate fillers. The bioactive material can be selected from bioactive glasses, silica gel, silica xerogels, silica aerogel, natrium silica glass, titanium gels, bioactive glass ionomer, hydroxyapatite, Ca/P-doped silica gel or the like. Any combination of said materials may naturally also be used. When rapid mineralization is needed, it is preferred to have bioactive glass with sol-gel processed silica particles on the surface of the prepreg. It is naturally possible to coat both surfaces of the fiber-matrix system by the bioactive filler material. It is to be noted that the surface part is indeed a coating-type surface part, i.e. that the bioactive filler material making up the surface part is at least partly but also at most partly embedded in said base part The surface part is thus also inside the base part but not fully inside it The surface part consists essentially of bioactive filler material that is in particle form. By particle form is meant spheres as well as any kind of irregular form, as long as the largest dimension of a particle is not over 50% larger than the second largest dimension of said particle.

Some suitable bioactive glasses for this use are for example those described in WO 96/21628 and the patent application EP 02079105.9.

The combination of a prepreg with bioactive filler coating according to this invention is also referred to as a hybrid composite. A requirement for the hybrid composite is that the bioactive filler particles are bound to the resin matrix of the prepreg. Part of the bioactive filler particles is penetrated into the resin matrix that attaches the fillers to the surface. Also, it is preferred that part of the bioactive filler particles is not penetrated into the resin matrix. This allows the bioactive particles to come into the contact with the surface that needs to mineralize.

When the prepreg is used, the matrix is still in its non- or partly cured form. This enables contouring and placing the prepreg according to the surface topography of teeth or cavity to be in good contact with the dentine. When the prepreg is used to cover the surface of the implant of metals, polymers or composites, it is also used in its non- or partly cured form. In this case, the prepreg is placed in contact with the surface of the implant and attached to it when the curing of the resin matrix of the prepreg occurs. Attachment of the composite to metal surface is obtained by micromechanical and chemical means. Attachment of the composite to polymer or composite implant is obtained by interpenetrating polymer networks or by chemical reaction, induced for example by free radical polymerization.

The fiber or fibers used in the composition may be any fiber known per se that is compatible with the matrix used and a person skilled in the art will be able to readily assess which fiber is the most suitable for the intended application.

The fibers may for example be selected from a group consisting of inert glass fibers (such as S or E glass), bioactive glass fibers, silica fibers, quartz fibers, ceramic fibers, carbon/graphite fibers, aramid fibers, ceramic fibers, poly(p-phenylene-2,6-benzobisoxazole) fibers (PBO), poly(2,6-diimidazo(4,5-b4',5'-e)pyridinylene-1,4(2,5-dihydro) phenylene fibers (PIPD), polyolefin fibers, fibers prepared from copolymers of olefins, polyester fibers, polyamide fibers, polyacrylic fibers, sol-gel processed silica fibers, collagen fibers, cellulose fibers and modified cellulose fibers. Any combination of said fibers may be used. Poly(p-phenylene-2,6-benzobisoxazole) fibers and poly(2,6-diimidazo(4,5-b4',5'-e)pyridinylene-1,4(2,5-dihydro)phenylene fibers belong to a group called rigid-rod polymer fibers. It is obvious to a person skilled in the art that any other known fibers may be used in the present invention, provided it is possible to obtain a suitable adhesion between said fibers and matrix, in order to achieve the desired mechanical properties. In dental applications the most suitable fibers are, at the moment of filing this specification, glass fibers due to their good cosmetic and esthetic properties and because the glass fibers allow light polymerization to be performed through the matrix band.

The fibers of the matrix band may be in any desired form, such as continuous fibers, chopped fibers or in the form of woven or nonwoven mat or sheet. The orientation of the fibers may be unidirectional, bidirectional, tridirectional, tetradirectional or have a random orientation. It is also possible to use for example both continuous unidirectional fibers and chopped, randomly oriented fibers.

According to an embodiment of the invention, the prepreg is X-ray opaque, i.e. radio-opaque. The X-ray opacity may be obtained by using metal particles or metal bands of fibers in the prepreg. These materials would naturally need to be biocompatibles.

The matrix of the prepreg may be made of any suitable monomer or polymer or mixture of them. The matrix of the prepreg is made of non-degradable, partly degradable or degradable polymers or their combinations.

The matrix of the prepreg may comprise monomers selected from the group consisting of methyl acrylate, ethyl acrylate, propyl acrylate, isopropyl acrylate, n-hexyl acrylate, styryl acrylate, allyl acrylate, methyl methacrylate, ethyl methacrylate, propyl methacrylate, isopropyl methacrylate, n-butyl methacrylate, isobutyl methacrylate, 2-ethylhexyl methacrylate, cyclohexyl methacrylate, isobornyl methacrylate, tetrahydrofurfuryl methacrylate, benzyl methacrylate, morpholinoethyl methacrylate, diurethane dimethacrylate, acetoacetoxy ethyl methacrylate (AAEM), methacrylate functionalized dendrimers, other methacrylated hyperbranched oligomers, hydroxymethyl methacrylate, hydroxymethyl acrylate, hydroxyethyl methacrylate, hydroxyethyl acrylate, hydroxypropyl methacrylate, hydroxypropyl acrylate, tetrahydrofurfuryl methacrylate, tetrahydrofurfuryl acrylate, glycidyl methacrylate, glycidyl acrylate, triethylene glycol diacrylate, tetraethylene glycol dimethacrylate, tetraethylene glycol diacrylate, trimethylolethane trimethacrylate, trimethylolpropane trimethacrylate, pentaerythritol trimethacrylate, trimethylolethane triacrylate, trimethylolpropane triacrylate, pentaerythritol triacrylate, pentaerythritol tetramethacrylate, pentaerythritol tetra-acrylate, ethylene dimethacrylate, ethylene diacrylate, ethylene glycol dimethacrylate, diethylene glycol dimethacrylate, triethylene glycol dimethacrylate (TEGDMA), ethylene glycol diacrylate, diethyleneglycol diacrylate, buthylene glycol dimethacrylate, buthylene glycol diacrylate, neopentyl glycol dimethacrylate, neopentyl glycol diacrylate, 1,3-butanediol dimethacrylate, 1,3-butanediol diacrylate, 1,4-butanediol dimethacrylate, 1,4-butanediol diacrylate, 1,6-hexanediol dimethacrylate, 1,6-hexanediol diacrylate, di-2-methacryloxyethyl-hexametylene dicarbamate, di-2-methacryloxyethyl-trimethylhexamethylene dicarbamate, di-2-methacryloxyethyl-dimethylbenzene dicarbamate, di-2-methacryloxyethyl-dimethylcyclohexane dicarbamate, methylene-bis-2-methacryloxyethyl-4-cyclohexyl carbamate, di-1-methyl-2-methacryloxyethyl-hexamethylene dicarbamate, di-1-methyl-2-methacryloxyethyl-trimethylhexamethylene dicarbamate, di-1-methyl-2-methacryloxyethyl-dimethylbenzene dicarbamate, di-1-methyl-2-methacryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-2-methacryloxyethyl-4-cyclohexyl carbamate, di-1-methyl-2-methacryloxyethyl-hexamethylene dicarbamate, di-1-methyl-2-methacryloxyethyl-trimethylhexamethylene dicarbamate, di-1-methyl-2-methacryloxyethyl-dimethylbenzene dicarbamate, di-1-methyl-2-methacryloxyethyl-dimethylcyclohexane dicarbamate, methylene-bis-1-methyl-2-methacryloxyethyl-4-cyclohexyl carbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-1-chloromethyl-2-methacryloxyethyl-4-cyclohexyl carbamate, 2,2-bis(4-(2-hydroxy-3-methacryloxy)phenyl)propane (BisGMA), 2,2'-bis(4-methacryloxyphenyl)propane, 2,2'-bis(4-acryloxyphenyl)propane, 2,2'-bis[4(2-hydroxy-3-acryloxyphenyl)propane, 2,2'-bis(4-methacryloxyethoxyphenyl)propane, 2,2'-bis(4-acryloxyethoxyphenyl)propane, 2,2'-bis(4-methacryloxypropoxyphenyl)propane, 2,2'-bis(4-acryloxypropoxyphenyl)propane, 2,2'-bis(4-methacryloxydiethoxyphenyl)propane, 2,2'-bis(4-acryloxydiethoxyphenyl)propane, 2,2'-bis[3(4-phenoxy)-2-hydroxypropane-1-methacrylate]propane, 2,2'-bis[3(4-phenoxy)-2-hydroxypropane-1-acrylate]propane and mixtures thereof.

The matrix may also be made of crosslinkable monomers or polymers such as ε-caprolactone, polycaprolactone, polylactides, polyhydroxyproline, and other biopolymers as well as polyamides, polyurethane, polyethylene, polypropylene, other polyolefins, polyvinyl chloride, polyester, polyether, polyethyleneglycol, polysaccharide, polyacrylonitrile, polymethyl methacrylate, phenol-formaldehyde, melamine-formaldehyde, and urea-formaldehyde. The matrix may naturally also consist of a mixture of a monomer(s) and a polymer(s).

Dendrimers having 5 to 35 functional groups such as methacrylate or acrylate groups may also be used. Multifunctionality forms highly cross-linked matrix and decreases the creep of the polymer in the long-term use. Examples of suitable dendrimers are given for example in U.S. Pat. No. 5,834,118 (incorporated herein by reference). Dendrimers may particularly be startburst or hyperbranched methacrylated polyesters.

According to an embodiment of the invention, the matrix is selected from the group consisting of triethylene glycol dimethacrylate, 2,2-bis(4-(2-hydroxy-3-methacryloxy)phenyl)propane, polymethyl methacrylate, methyl methacrylate, hydroxyethyl methacrylate, urethan dimethacrylate, starburst methacrylated polyesters, hyperbranched methacrylated polyesters, polyvinyl chloride, polyetherketone, polylactides, ε-caprolactone, poly-OH-proline and mixtures thereof.

A typical polymer in dental applications at the moment of filing this specification is polymethyl methacrylate (PMMA), especially PMMA having a molecular weight between 13 000 and 996 000 g/mol. More preferably the molecular weight is between 20 000 and 300 000 g/mol, such a molecular weight allowing an especially easy formation of a dense polymer matrix for the finished composite. It is for example suitable to use dimethacrylates in combination with polymethyl methacrylate as a resin matrix, because together they form a gel like matrix before curing. It is naturally also possible to use mixtures of PMMA's having different molecular weights.

The curing of the prepreg according to the present invention is performed by a known curing process suitable for the selected matrix. The curing may be induced for example by electromagnetic radiation selected from the group consisting of visible light, ultra-violet light, blue light and laser irradiation. Curing of the matrix of the prepreg may also be made with any of the conventionally used initiator—catalysts systems. Among many of them, photosensitive camphorquinone—amine initiator system is preferred in dental applications. In endosseus implant coatings, benzoylperoxide systems can be used. Also other radical formation means can be used. During curing, the matrix adapts the surface topography of the tooth or the implant surface and becomes attached to the surface.

According to another embodiment, said matrix is autopolymerizable and the curing is induced by applying an activator on the matrix band. It is also possible to use matrixes that are stored in low temperatures (under room temperature or below 0° C.) after manufacturing and that autopolymerize once the temperature is increased to room temperature. The preferable curing initiation is obtained by radiation with blue light or by laser by help of initiators and activators for the polymerization and/or crosslinking. Thickness of the prepreg according to the invention may vary between 0.01 mm and 10 mm. In applications of treatment for hypersensitive dentine, prepreg thickness of 0.04 to 0.2 mm is preferred. In basement fillings, prepreg thickness of 1.0 to 3.0 mm is preferred. In applications of endosseus implants, it is preferred to use bioactive glass fibers in combination of biostable glass fibers in the prepreg. The prepreg thickness in these applications is preferably from 1.0 to 10.0 mm. In root canal applications of root fillings or root canal posts, the prepreg consists preferably of continuous unidirectional fibers. The diameter of the prepreg may vary from 0.1 to 4.0 mm.

The invention further relates to a composite obtainable by curing the prepreg according to the invention. The composite so obtained may be used in any of the applications herein mentioned for the prepreg.

The invention also relates to a mineralizing sheet for treatment of hypersensitive teeth, said sheet being characterized in that it consists essentially of a supporting sheet having two opposing faces, a first of said faces being at least partially covered by a prepreg according to the present invention or by a composite according to the present invention. Preferably, said first face is partially covered by a prepreg or a composite in such a manner that the edges of said supporting sheet are essentially free from said prepreg or composite. This makes it easier to attach the supporting sheet to the tooth or teeth to be treated. Typically, about 0.5-3 mm, preferably 1-2 mm of the edges is free from prepreg or composite. The supporting sheet may also be attached to the tooth to be treated through the prepreg or composite, at least to some extent.

The mineralizing sheet may also have an antibacterial effect when a bioactive polymer having an antibacterial effect is used, for example.

The invention still relates to the prepreg according to the invention for use as treatment material for hypersensitive teeth (mineralization material), basement filling material for tooth restorations such as fillings, root canal fillings and posts, cores of dental crowns, clasps, retainers of removable dentures, tooth mineralizing splints, periodontal splints, occlusal splints, cervical splints, replacement of bones, coatings of implants, in endosseus implants, in replacement of bones, support of bone fractures, bone fillings, tissue guiding materials, coatings of implants, artificial parts of jawbones and in other applications where bioactive composites are needed. In all the possible uses, the reinforcing property of the present prepreg (and composite) is important It is for example possible to use the present invention to support hyper mobile teeth.

In the case of treatment of hypersensitive dentine, the prepreg forms a coating for the hypersensitive tooth surface. The fiber part of the prepreg protects the bioactive fillers and retains them on place in contact to the hypersensitive dentine for the mineralization of the dentine tubules to occur. The use of degradable polymers with degradable bioactive glass fibers or sol-gel processed silica fibers is preferred when hypersensitive dentine is treated. For this application, it preferred that the materials degrade with time, and removal of the materials is by dental professionals is not necessarily needed.

In the case of using the prepreg as a basement filling material of tooth restorations, the prepreg is covered with a layer of restorative filling composite to achieve polishable and wear resistance surface. The prepreg may be cured either alone, i.e. before the application of the filling material, or together with the filling material. The restorative composite layer is attached to the prepreg as basement filling material for example by polymerization or crosslinking (i.e. chemical bonding) or by interpenetrating polymer network (i.e. mechanical bonding). The intention of the prepreg/composite basement filling material is to allow mineralization of the dentine to occur under the filling. This protects the pulp of the tooth from microbes, toxins and effects of changes of osmotic pressure or temperature changes. It also improves bonding of the fining material to dentine by hardening the dentine surface. The antimicrobial effect of the bioactive fillers inhibits oral microbes to grow at the interphase of filling and tooth.

The prepreg basement filling material of tooth restorations reinforces the fling-tooth system. This is made by the reinforcing fibers of the fiber part of the prepreg that offers better strength properties for the filling than those of the restorative filling composite only.

In the case of tooth mineralizing splints, periodontal splints, occlusal splints and cervical splints, it is possible to include said bioactive material only in the position needed, for example such that when said splint is used, the bioactive material comes into contact only with the cervix dentis. It is also possible to include an indicator that shows when the bioactive material needs to be changed. Such an indicator may for example be a color indicator.

In the case of coating of implants, such as fiber-reinforced composite implants, the prepreg and especially the fiber part of the prepreg binds the reinforcing fibers of the core of the implant together. This improves resistance to delamination and resistance to torque forces of the composite implant The bioactive outer surface allows new bone to attach to the surface by means of mineralization.

In the case of using the hybrid composite in replacement of long bone or jawbone, the prepreg is placed over or close-by the remaining parts of bone, surrounded around the parts of the bone and cured. After curing, the thus formed composite forms support of the pieces of bone and the bioactive granules allow mineralization to occur on the surface of the composite. The hybrid composite according to the present invention may also be used as a bone filling material in wedge osteothomy and arthritic joints. It is also possible to manufacture a device comprising a supporting sheet and a desired amount of the present hybrid prepreg or composite in a desired shape, for use in the filling of a bone cavity, for example. In the case of using the hybrid composite according to the present invention as temporary or permanent root canal filling or post, the prepreg is placed into the root canal. During insertion of the post to the canal, the bioactive glass granules become into contact with dentine and start to mineralize and disinfect the dentine. During curing, the prepreg forms a solid root canal filling or post.

In the case of temporary root canal filing, the filling is removed after disinfection has occurred.

The invention also relates to the use of a prepreg according to the invention for the manufacturing of a dental restoration, root canal post, a dental crown, a retainer for removable denture, a tooth mineralizing splint, an occulusal splint, a cervical splint, a clasp and a coated implant.

In a more general manner, the invention relates to the use of a prepreg and a composite according to the present invention in dental and medical applications, such as those mentioned above, typically for treatment material for hypersensitive teeth, basement filling material for tooth restorations, root canal posts, cores of dental crowns; clasps, retainers of removable dentures, tooth mineralizing splints, occlusal splints, cervical splints, replacement of bones, support of the bone fractures, bone fillings, tissue guiding materials and coatings of implants.

The prepreg according to present invention may for example be used in the fabrication of a device for treatment of hypersensitive dentine. For example, a prepreg made with the technique described in U.S. Pat. No. 6,197,410 (incorporated herein by reference) can be coated with a powder of bioactive glass granules having a grain size of 0.5 to 40 μm. The fibers may be the form of woven fibers with a weave thickness of 0.06 mm. The polymer-monomer gel wetting resin of the prepreg is then used to bound the bioactive granules to the surface. The marginal areas of the prepreg are preferably left without bioactive glass coating in order to leave the marginal surface to bond to tooth surface. If the polymer matrix of the prepreg is light sensitive, the formed prepreg should be packed to light impermeable package.

When the prepreg is then used, the cleaned hypersensitive dentine surface is covered with the prepreg by pressing the bioactive surface against the dentine. The prepreg is then light cured with a dental light-curing device and the formed composite is subsequently attached to the tooth surface. During the next 15 to 30 days, the bioactive glass biomineralizes the dentine surface and eliminates the symptoms of hypersensitive dentine. The composite is thereafter removed.

The prepreg according to the present invention may further be used in the fabrication of a basement filling of tooth restorations. A prepreg as described above with randomly oriented fibers is coated with bioactive glass granules on one surface. When the restoration is made, the prepreg with bioactive surface is pressed against the bottom of the cavity, namely against the dentine. The prepreg is cured with appropriate dental curing unit. The formed composite layer may then be covered with conventional dental restorative paste. The formed composite under the restorative composite remains as integral part of the restoration, reinforcing the restorative filling composite.

The prepreg according to the present invention may still further be used in the coating of an implant. A prepreg as described above with randomly oriented fibers is coated with bioactive glass granules on one side of the prepreg. The non-coated side is then pressed against the implant surface of titanium, cobalt-chromium alloy or non-biodegradable composite. The matrix of the prepreg is attached to the implant surface during curing of the matrix of the prepreg.

The prepreg according to the present invention may yet further be used as replacement of a part of a long bone. The prepreg manufactured as described above may be placed around the ends of a bone fragment in surgical operation. The prepreg is then cured by for example light activation and the thus formed composite forms a solid tube-like capsule that attaches the pieces of bone together. The bioactive granules on the surface of the composite enables biomineralization to occur and behave as bone conductive surface.

The prepreg according to the present invention may also be used as temporary or permanent root canal filling or root canal post. The prepreg preferably contains continuous unidirectional fibers and when the prepreg has been inserted into the root canal, the bioactive glass particles start to mineralize and disinfect the dentine. When the prepreg is cured, it forms a solid fiber reinforced composite root canal post which is used for retention of an artificial crown.

In this specification, except where the context requires otherwise, the words "comprise", "comprises" and "comprising" means "include", "includes" and "including", respectively. That is, when the invention is described or defined as comprising specified features, various embodiments of the same invention may also include additional features. Also, the reference signs should not be construed as limiting the claims.

The invention is described below in greater detail by the following, non-limiting drawings.

DETAILED DESCRIPTION OF THE DRAWINGS

Figure 1A:
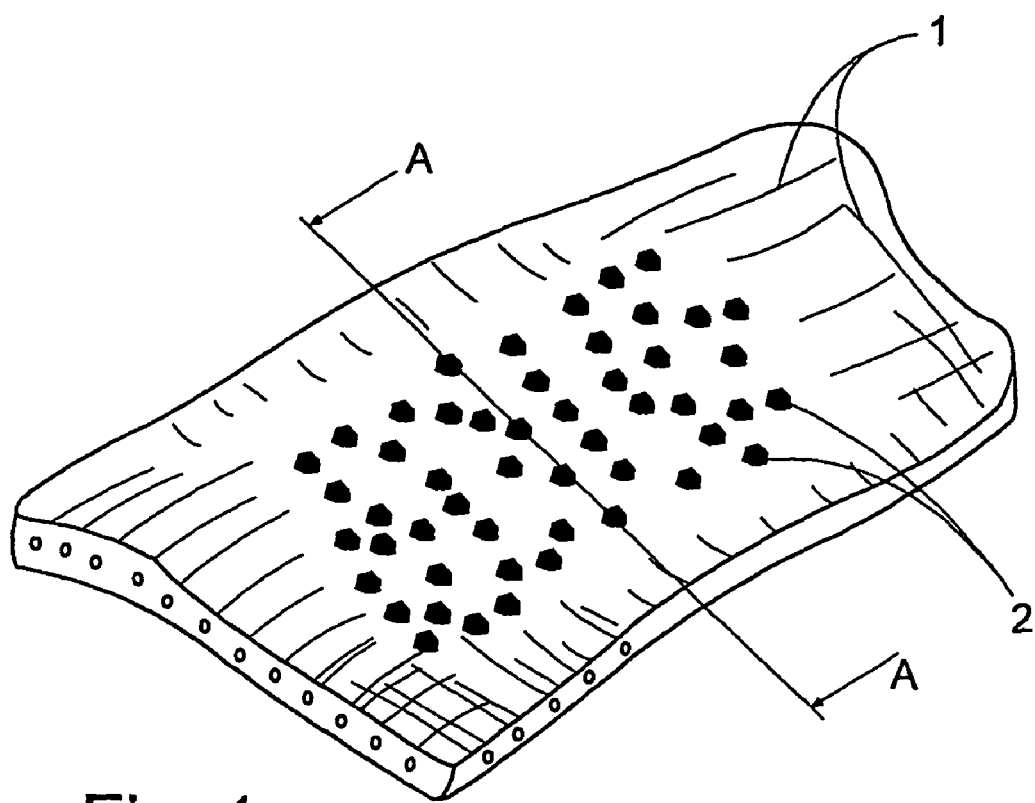
FIG. 1a illustrates schematically the structure of a prepreg according to a first embodiment of the present invention.
Figure 1B:
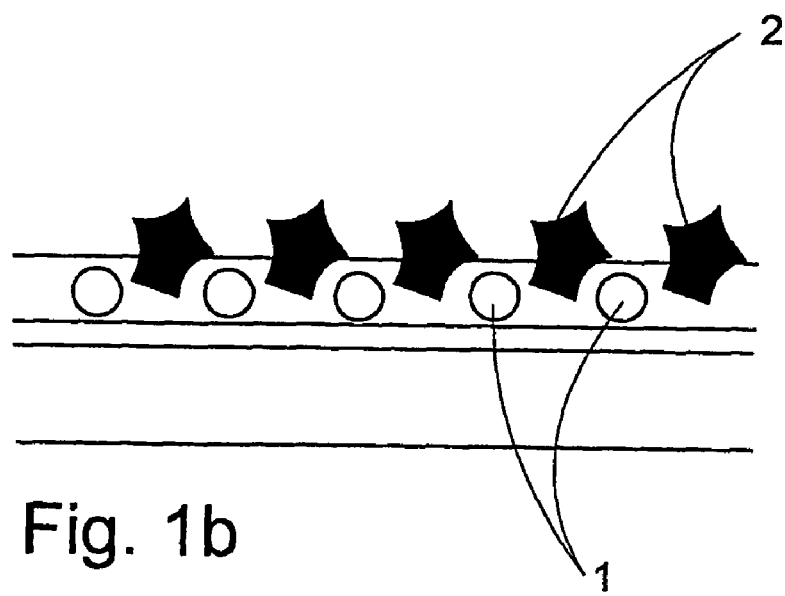
FIG. 1b shows a cross-sectional view of the structure illustrated in FIG. 1a, along the line A-A.

FIGS. 1a and 1b illustrate schematically the structure of a prepreg according to a first embodiment of the present invention. The prepreg consists of a woven mat 1, embedded in a partly uncured matrix and of a coating of bioactive particulate fillers 2. FIG. 1b shows a cross-sectional view of the structure illustrated in FIG. 1a, along the line A-A.

Figure 2A:
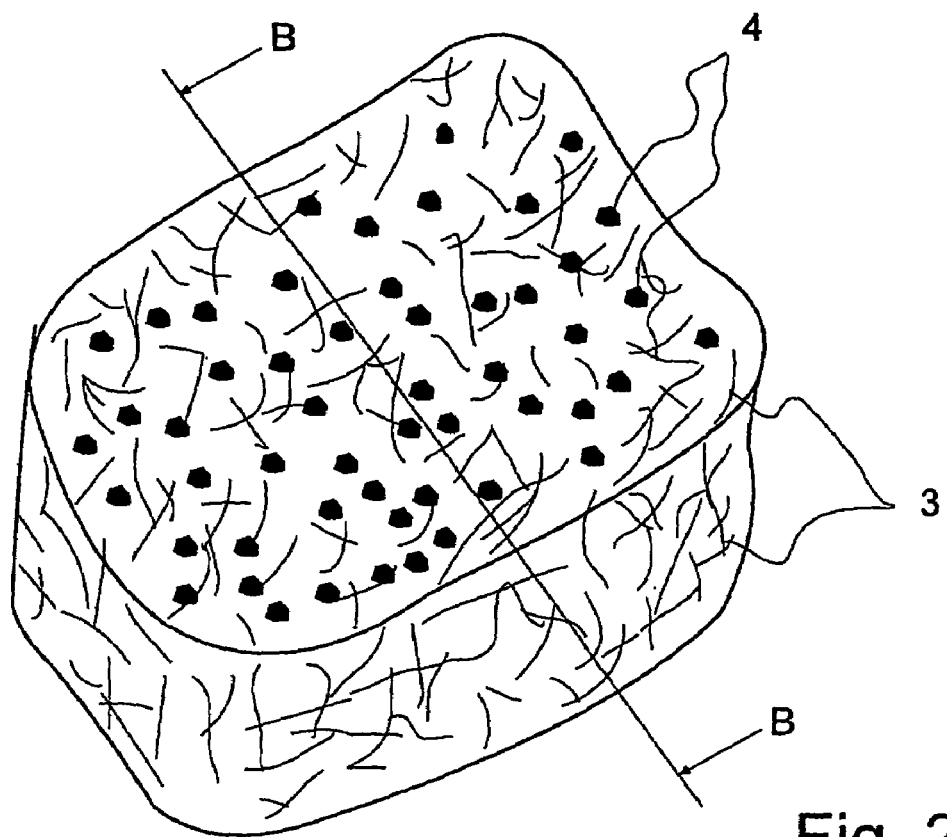
FIG. 2a illustrates schematically the structure of a prepreg according to a second embodiment of the present invention.
Figure 2B:
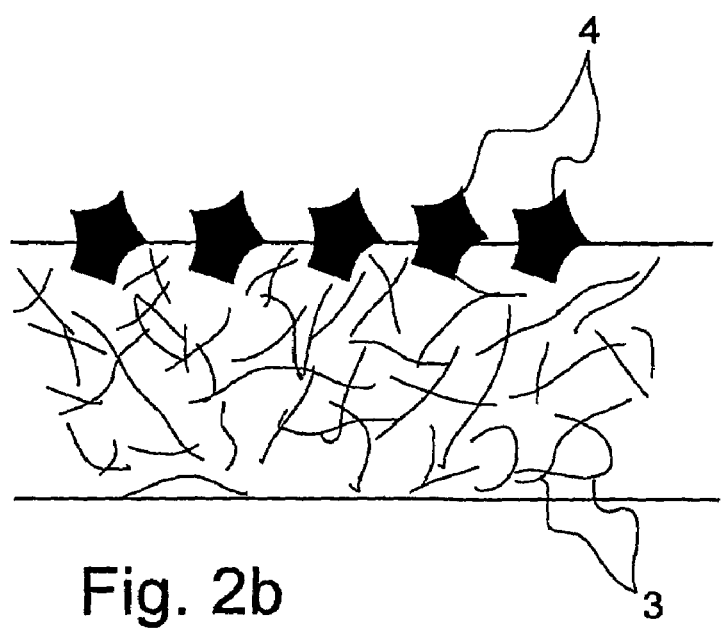
FIG. 2b shows a cross-sectional view of the structure illustrated in FIG. 2a, along the line B-B.

FIGS. 2a and 2b illustrate schematically the structure of a prepreg according to a second embodiment of the present invention. The prepreg consists of chopped fibers 3, embedded in a partly uncured matrix and of a coating of bioactive particulate fillers 4. FIG. 2b shows a cross-sectional view of the structure illustrated in FIG. 2a, along the line B-B.

Figure 3A:
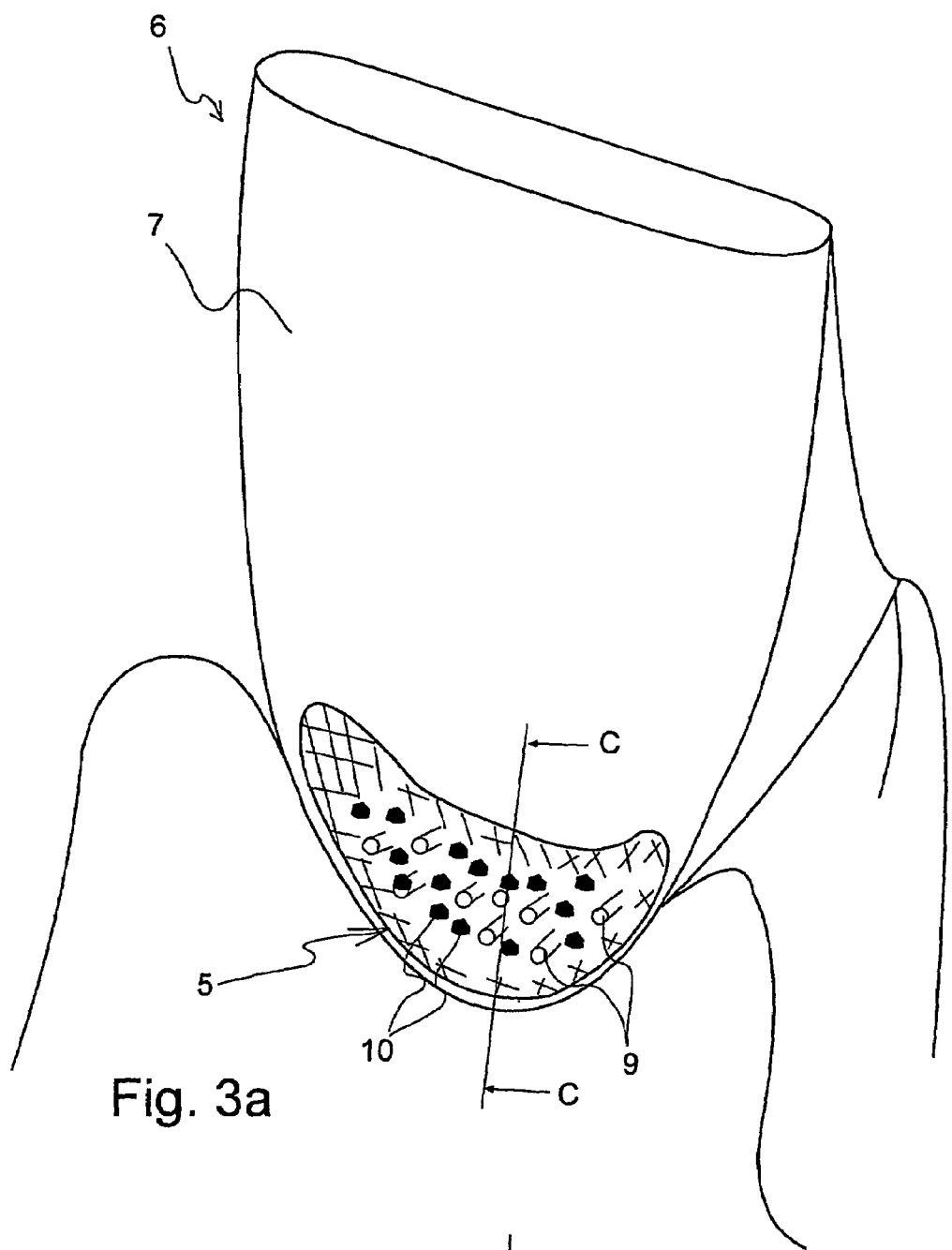
FIG. 3a illustrates the use of the prepreg according to a third embodiment of the invention.
Figure 3B:
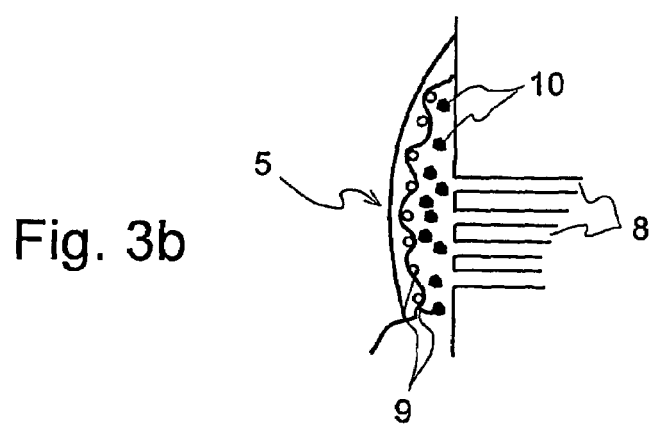
FIG. 3b shows a partial cross-sectional view of the use illustrated in FIG. 3a, along the line C-C.

FIGS. 3a and 3b illustrate the use of the prepreg according to a third embodiment of the invention, wherein FIG. 3b shows a partial cross-sectional view of the use illustrated in FIG. 3a, along the line C-C. These Figures illustrate a mineralizing sheet for treatment of hypersensitive teeth according to the present invention. The prepreg 5 is used on a tooth's 6 surface 7 having exposed dentinal tubules 8, meaning the hypersensitiveness of the tooth. The prepreg consists of a woven mat 9 embedded in a matrix and of a coating of bioactive particulate fillers 10. The prepreg is positioned on the tooth's 6 surface 7 such that the bioactive filler 10 coating is placed into contact with the surface 7.

Figure 4:
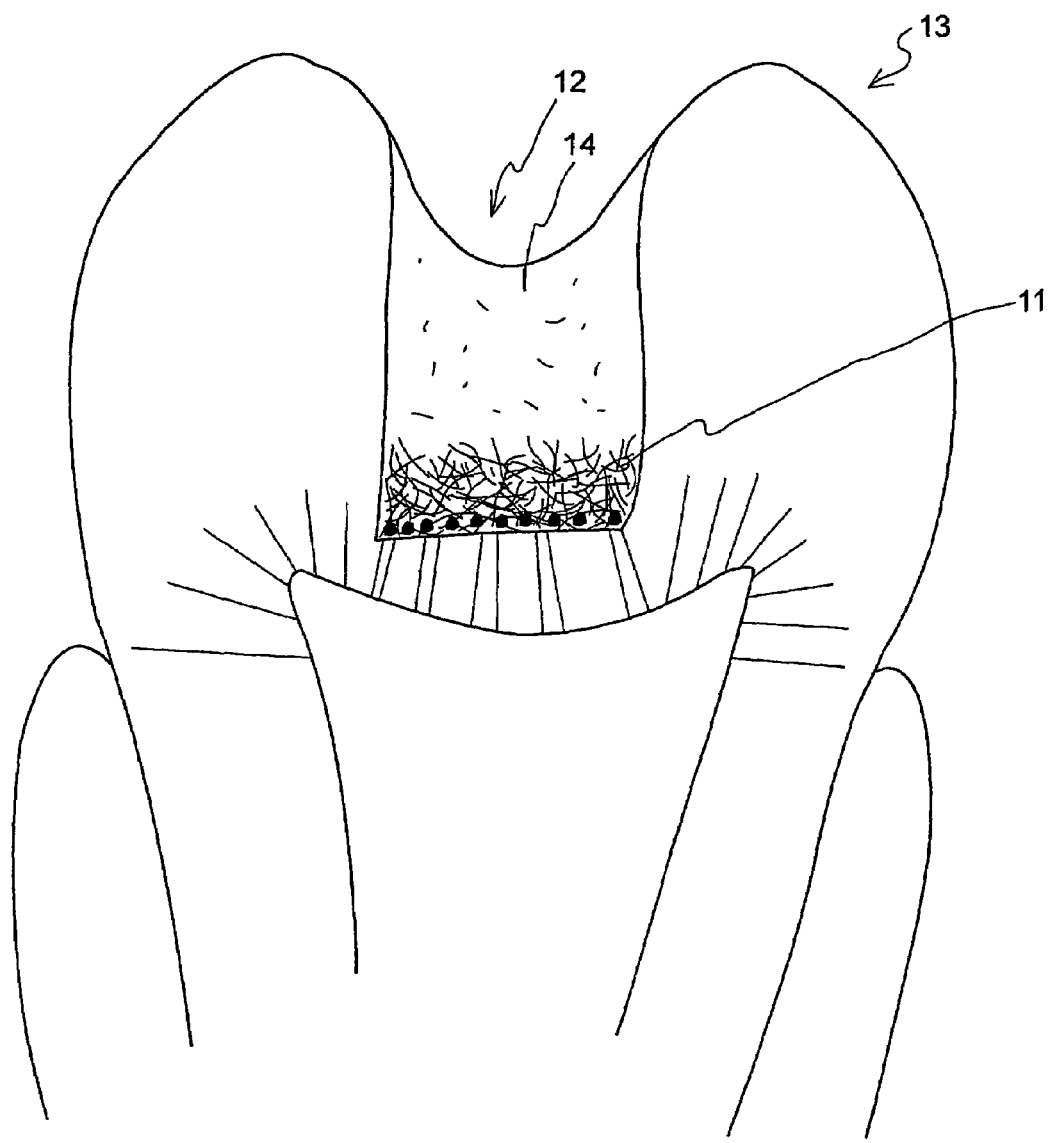
FIG. 4 illustrates the use of the prepreg according to a fourth embodiment of the invention.

FIG. 4 illustrates the use of the prepreg according to a fourth embodiment of the invention. The prepreg 11 is used as a basement filling material in a cavity 12 of tooth 13 underneath of restorative filling material 14.

Figure 5:
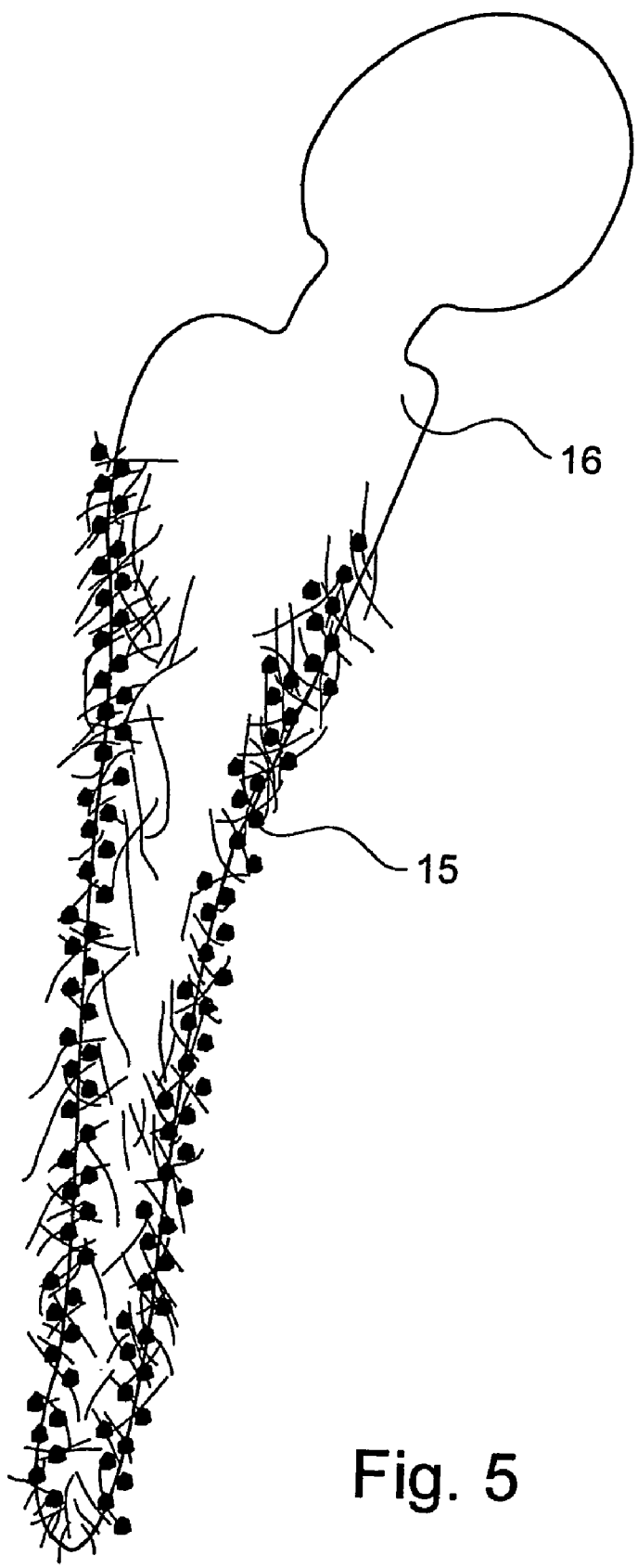
FIG. 5 illustrates the use of the prepreg according to a fifth embodiment of the invention.

FIG. 5 illustrates the use of the prepreg according to a fifth embodiment of the invention. The cured prepreg, i.e. the composite 15 is used as a coating of endosseus implant 16, thus allowing the bone to mineralize to the surface of the composite 15.

Figure 6:
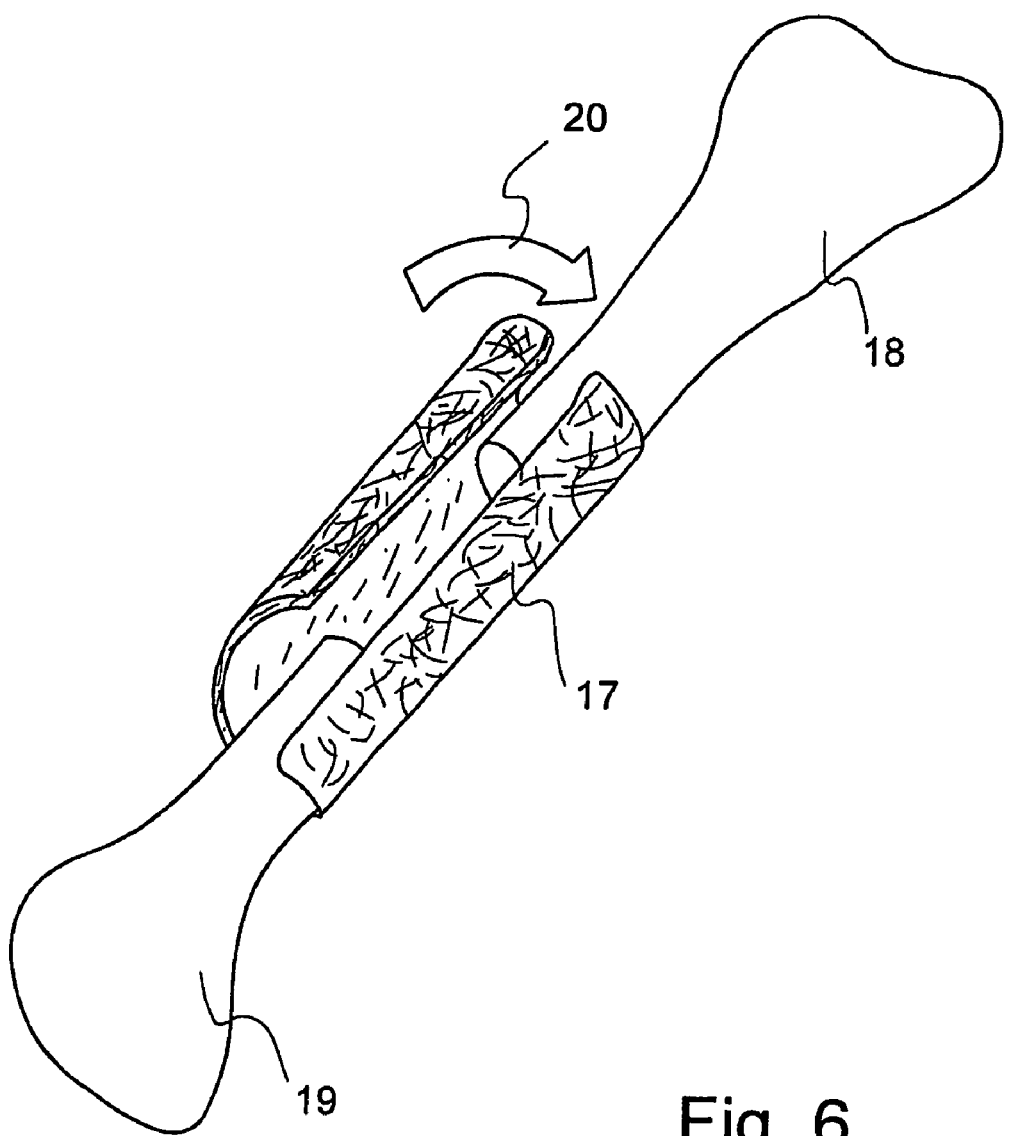
FIG. 6 illustrates the use of the prepreg according to a sixth embodiment of the invention.

FIG. 6 illustrates the use of the prepreg according to a sixth embodiment of the invention. The composite is used as support and replacement part of a long bone cut into two pieces 18 and 19, thus allowing the bone to grow within the surface of the composite. The prepreg 17 is represented as being enveloped around the pieces 18 and 19, in the direction of the arrow 20.

Figures 7A, 7B:
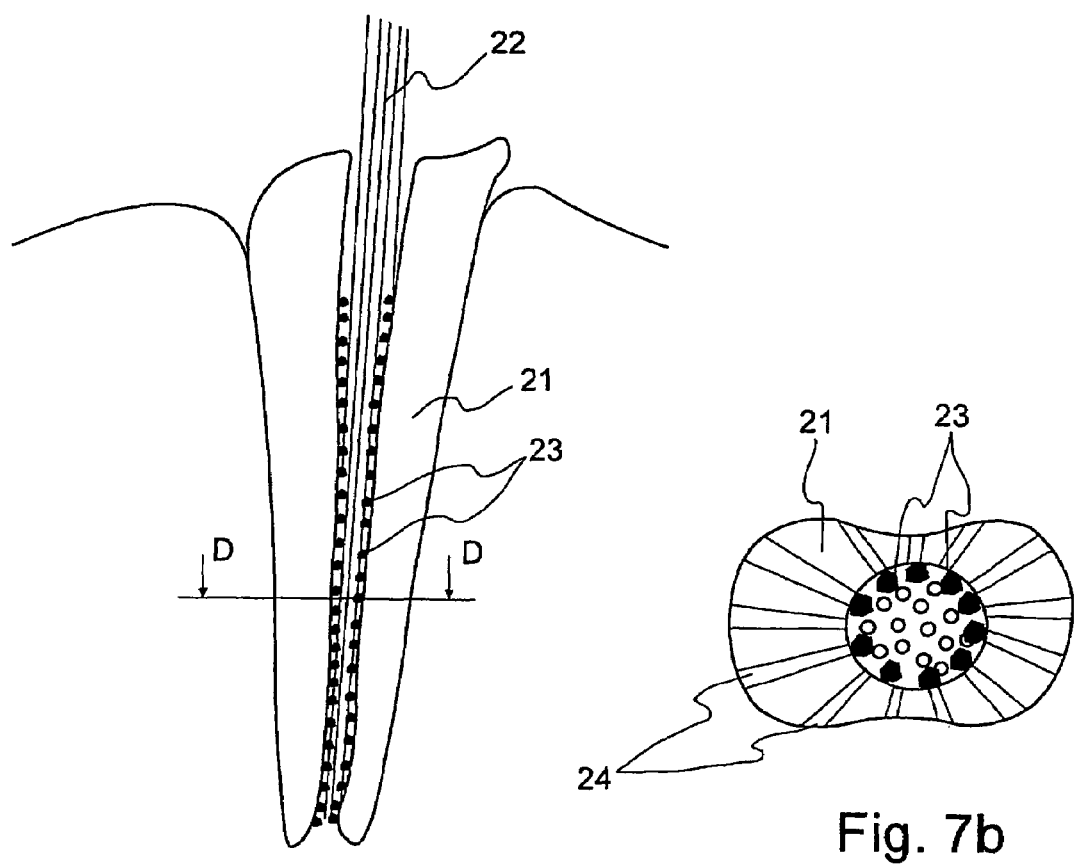
FIG. 7a illustrates the use of the prepreg according to a seventh embodiment of the invention.
FIG. 7b shows a cross-sectional view of the use illustrated in FIG. 7a, along the line D-D.

FIG. 7a illustrates the use of the prepreg according to a seventh embodiment of the invention. The prepreg is used as root canal filling and post. The root (21) is filled with the prepreg (22) having bioactive glass granule (23) particles on its surface. FIG. 7b shows a cross-sectional view of the use illustrated in FIG. 7a, along the line D-D. The Figure shows the root (21), its dentine tubules (24) that are mineralized and disinfected by the granules of bioactive glass (23).

The invention claimed is:

1. A prepreg comprising a base part, said base part comprising fibers and a matrix, said matrix being at least partially uncured, wherein it further comprises at least one surface part consisting essentially of bioactive filler material, said bioactive filler material being in particle form and partially embedded in said base part.

2. A prepreg according to claim 1, wherein said bioactive filler material is selected from the group consisting of bioactive glass, silica gel, titanium gel, silica xerogel, silica aerogel, sodium silica glass, bioactive glass ionomer, hydroxyapatite, Ca/P-doped silica gel and mixtures thereof.

3. Prepreg according to claim 1 wherein said fibers are selected from the group consisting of inert glass fibers, bioactive glass fibers, silica fibers, quartz fibers, ceramic fibers, carbon/graphite fibers, aramid fibers, ceramic fibers, poly(p-phenylene-2,6-benzobisoxazole) fibers, poly(2,6-diimidazo (4,5-b4',5'-e)pyridinylene-1,4(2,5-dihydro)phenylene fibers, polyolefin fibers, fibers prepared from copolymers of olefins, polyester fibers, polyamide fibers, polyacrylic fibers, sol-gel processed silica fibers, collagen fibers, cellulose fibers, and mixtures thereof.

4. Prepreg according to claim 1, wherein said fibers are in a form selected from the group consisting of continuous fibers, chopped fibers, mat, sheet or mixtures thereof, and wherein they are oriented in one, two, three or four directions, randomly or mixtures thereof.

5. Prepreg according to claim 1, wherein said matrix is selected from the group consisting of triethylene glycol dimethacrylate, 2,2-bis(4-(2-hydroxy-3-methacryloxy)phenyl)propane, polymethyl methacrylate, methyl methacrylate, hydroxyethyl methacrylate, urethan dimethacrylate, starburst methacrylated polyesters, hyperbranched methacrylated polyesters, polyvinyl chloride, polyetherketone, polylactides, ε-caprolactone, polyhydroxyproline and mixtures thereof.

6. Prepreg according to claim 1, wherein it is X-ray opaque.

7. A composite obtained by curing the prepreg according to claim 1.

8. A mineralizing sheet for treatment of hypersensitive teeth, wherein it consists essentially of a supporting sheet having two opposing faces, a first of said faces being at least partially covered by a prepreg according to claim 1.

9. A mineralizing sheet for treatment of hypersensitive teeth, wherein it consists essentially of a supporting sheet having two opposing faces, a first of said faces being at least partially covered by a composite obtained by curing the prepreg according to claim 1.

10. The prepreg of claim 1, wherein said bioactive filler material comprises bioactive glass granules having a particle size of from 0.5 to 40 μm.

11. The prepreg of claim 1, wherein said bioactive filler material comprises bioactive glass granules and sol-gel processed silica particles.

* * * * *